US011350846B2

(12) United States Patent
Rulkov et al.

(10) Patent No.: US 11,350,846 B2
(45) Date of Patent: Jun. 7, 2022

(54) IMPEDANCE REFLECTOR DETECTION SYSTEMS AND METHODS FOR USING THEM

(71) Applicant: CIANNA MEDICAL, INC., Aliso Viejo, CA (US)

(72) Inventors: Nikolai Rulkov, San Diego, CA (US); John E. Greene, Valley Center, CA (US)

(73) Assignee: Cianna Medical, Inc., Aliso Viejo, CA (US)

(*) Notice: Subject to any disclaimer, the term of this patent is extended or adjusted under 35 U.S.C. 154(b) by 730 days.

(21) Appl. No.: 16/152,289

(22) Filed: Oct. 4, 2018

(65) Prior Publication Data

US 2019/0117112 A1 Apr. 25, 2019

Related U.S. Application Data

(60) Provisional application No. 62/568,208, filed on Oct. 4, 2017.

(51) Int. Cl.

| | |
|---|---|
| ***A61B 5/06*** | (2006.01) |
| ***A61B 90/00*** | (2016.01) |
| ***A61B 5/00*** | (2006.01) |
| *A61B 34/20* | (2016.01) |
| *A61B 17/00* | (2006.01) |
| *A61B 90/30* | (2016.01) |

(52) U.S. Cl.

CPC ............ *A61B 5/063* (2013.01); *A61B 5/0093* (2013.01); *A61B 5/064* (2013.01); *A61B 90/39* (2016.02); *A61B 2017/00867* (2013.01); *A61B 2034/2051* (2016.02); *A61B 2090/306* (2016.02); *A61B 2090/309* (2016.02); *A61B 2090/397* (2016.02); *A61B 2090/3908* (2016.02); *A61B 2090/3966* (2016.02); *A61B 2090/3975* (2016.02); *A61B 2090/3987* (2016.02)

(58) Field of Classification Search

CPC ........... A61B 5/06; A61B 5/061; A61B 5/063; A61B 5/064; A61B 5/0093; A61B 90/39; A61B 2090/3904; A61B 2090/3908; A61B 2090/397; A61B 2090/3975; A61B 2090/3979

See application file for complete search history.

(56) References Cited

U.S. PATENT DOCUMENTS

2014/0309522 A1* 10/2014 Fullerton ............. A61B 5/4312 600/424

* cited by examiner

*Primary Examiner* — Carrie R Dorna

(74) *Attorney, Agent, or Firm* — Dorsey & Whitney LLP

(57) ABSTRACT

An impedance reflector apparatus, systems, and methods are provided for detecting a marker implanted within tissue that includes a switch for changing a configuration of an antenna of the marker. The apparatus includes a set of transmit electrodes coupled to a signal generator for transmitting a drive current into tissue to generate an electromagnetic field around the marker, a set of receive electrodes configured to detect voltage signals within the tissue corresponding to the electromagnetic field, and a light source for delivering light pulses into the body to open and close the switch to change the configuration of the antenna of the marker. A processor coupled to the receive electrodes processes the detected voltage signals to identify changes in the electromagnetic field that are synchronized with the light pulses to determine whether the marker is operating properly.

26 Claims, 9 Drawing Sheets

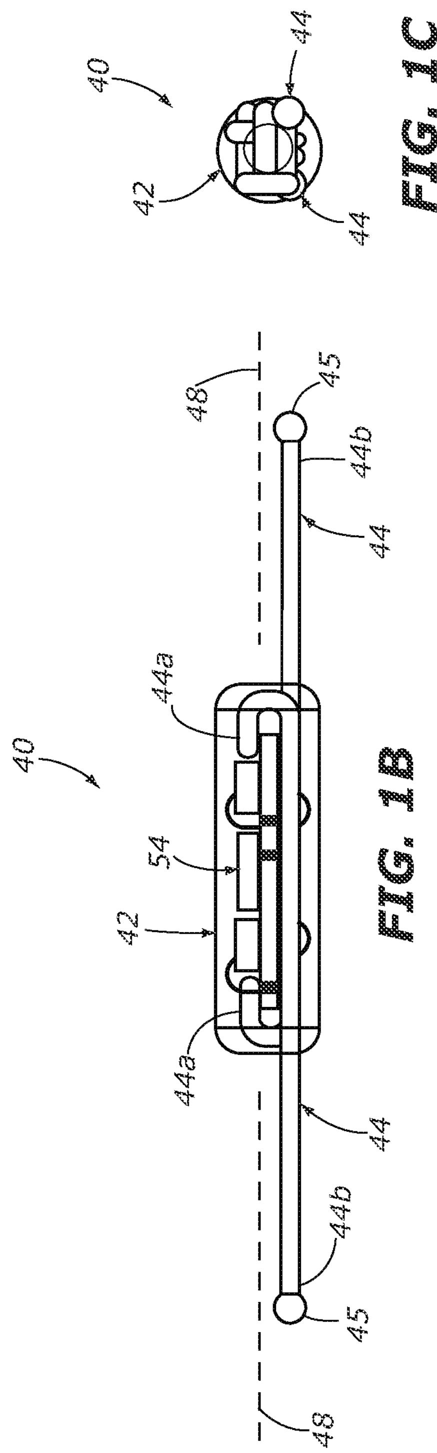
40
42
44
44
FIG. 1C
40
48
45
44b
44
44a
54
42
44a
44
44b
45
48
FIG. 1B
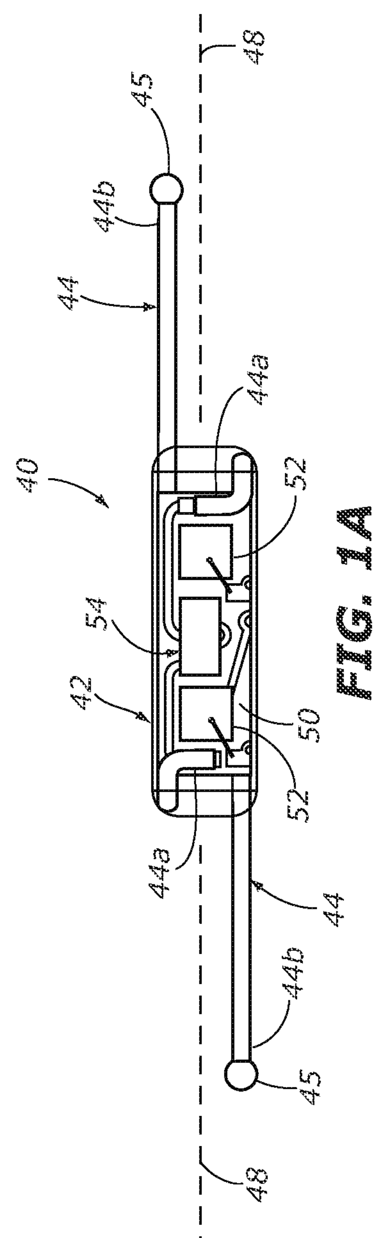
48
45
44b
44
44a
40
52
54
42
50
52
44a
44
44b
45
48
FIG. 1A

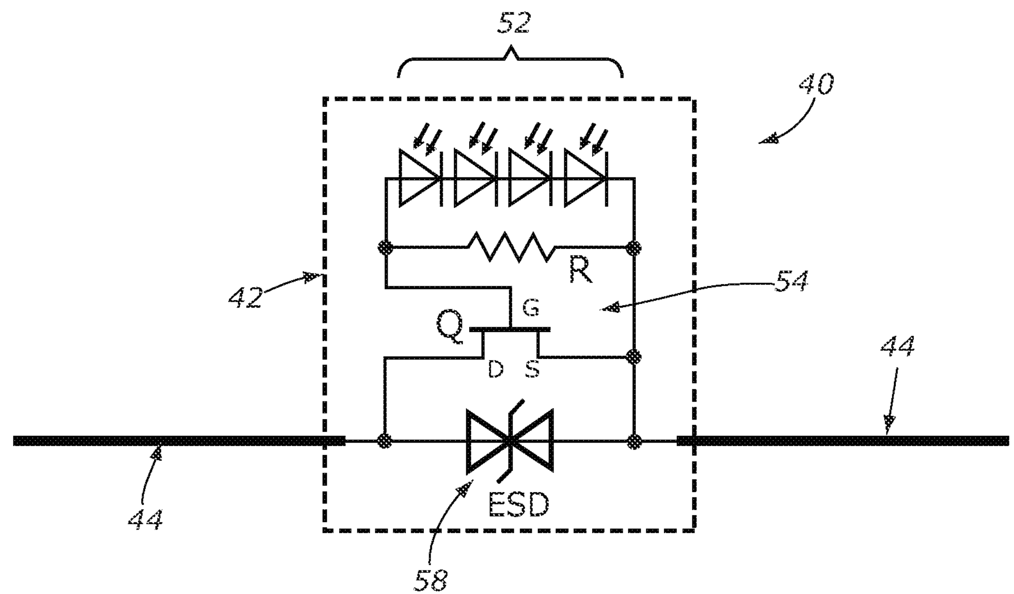
FIG. 2
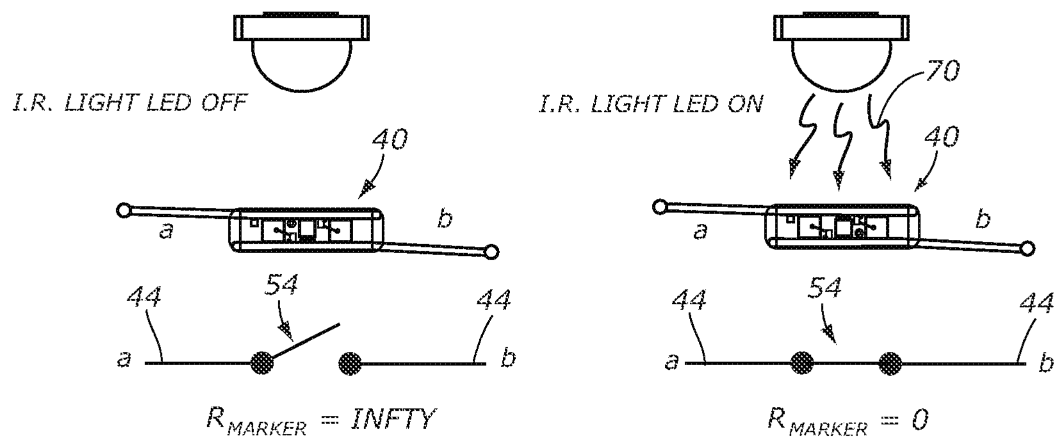
FIG. 3A
FIG. 3B

IMPEDANCE REFLECTOR DETECTION SYSTEMS AND METHODS FOR USING THEM

RELATED APPLICATION DATA

The present application claims benefit of provisional application Ser. No. 62/568,208, filed Oct. 4, 2017, and is related to Ser. No. 14/934,019, filed Nov. 5, 2015, which claims benefit of provisional application Ser. No. 62/171,804, filed Jun. 5, 2015. The entire disclosures of these applications and any references cited therein are expressly incorporated by reference herein.

FIELD OF THE INVENTION

The present invention relates generally to implantable markers or tags, and to systems and methods for detecting and/or localizing such markers within a patient's body, e.g., during surgical procedures or other procedures, such as during lumpectomy procedures, and, more particularly, to impedance reflector detection systems for detecting and/or identifying such markers.

BACKGROUND

Before a biopsy or surgical procedure to remove a lesion within a breast, e.g., during a lumpectomy procedure, the location of the lesion must be identified. For example, mammography or ultrasound imaging may be used to identify and/or confirm the location of the lesion before the procedure. The resulting images may be used by a surgeon during the procedure to identify the location of the lesion and guide the surgeon, e.g., during dissection to access and/or remove the lesion. However, such images are generally two dimensional and therefore provide only limited guidance for localization of the lesion since the breast and any lesion to be removed are three-dimensional structures. Further, such images may provide only limited guidance in determining a proper margin around the lesion, i.e., defining a desired specimen volume to be removed.

To facilitate localization, immediately before a procedure, a wire may be inserted into the breast, e.g., via a needle, such that a tip of the wire is positioned at the location of the lesion. Once the wire is positioned, it may be secured in place, e.g., using a bandage or tape applied to the patient's skin where the wire emerges from the breast. With the wire placed and secured in position, the patient may proceed to surgery, e.g., to have a biopsy or lumpectomy performed.

One problem with using a wire for localization is that the wire may move between the time of placement and the surgical procedure. For example, if the wire is not secured sufficiently, the wire may move relative to the tract used to access the lesion and consequently the tip may misrepresent the location of the lesion. If this occurs, when the location is accessed and tissue removed, the lesion may not be fully removed and/or healthy tissue may be unnecessarily removed. In addition, during the procedure, the surgeon may merely estimate the location of the wire tip and lesion, e.g., based on mammograms or other images obtained during wire placement, and may proceed with dissection without any further guidance. Again, since such images are two dimensional, they may provide limited guidance to localize the lesion being treated or removed.

Alternatively, it has been suggested to place a radioactive seed to provide localization during a procedure. For example, a needle may be introduced through a breast into a lesion, and then a seed may be deployed from the needle. The needle may be withdrawn, and the position of the seed may be confirmed using mammography. During a subsequent surgical procedure, a hand-held gamma probe may be placed over the breast to identify a location overlying the seed. An incision may be made and the probe may be used to guide excision of the seed and lesion.

Because the seed is delivered through a needle that is immediately removed, there is risk that the seed may migrate within the patient's body between the time of placement and the surgical procedure. Thus, similar to using a localization wire, the seed may not accurately identify the location of the lesion, particularly, since there is no external way to stabilize the seed once placed. Further, such gamma probes may not provide desired precision in identifying the location of the seed, e.g., in three dimensions, and therefore may only provide limited guidance in localizing a lesion.

Accordingly, apparatus and methods for localization of lesions or other tissue structures in advance of and/or during surgical, diagnostic, or other medical procedures would be useful.

SUMMARY

The present invention is directed to implantable markers and tags, and to systems and methods for detecting and/or localizing such markers within a patient's body, e.g., during surgical procedures or other procedures, such as during lumpectomy procedures. More particularly, the present invention is directed to impedance reflector detection systems for detecting and/or identifying markers within a patient's body and to methods for using such systems.

In accordance with one embodiment, an apparatus is provided for detecting a marker implanted within tissue that includes an energy converter coupled to a circuit for changing a configuration of an antenna of the marker that includes a set of transmit electrodes coupled to a signal generator for transmitting a drive current into tissue around the marker; a set of receive electrodes configured to detect voltage signals within the tissue corresponding to impedance of the tissue in response to the drive current; a light source for delivering light pulses into the body to cause the energy converter to activate and deactivate the circuit to change the configuration of the antenna of the marker; and a processor coupled to the receive electrodes for processing the voltage signals to identify changes in the impedance that are synchronized with the light pulses to determine whether the marker is operating properly.

In accordance with another embodiment, a system is provided for localization of a target tissue region within tissue that includes a marker sized for implantation within tissue comprising an energy converter coupled to a circuit for changing a configuration of an antenna of the marker; and a impedance reflector apparatus. The apparatus may include a set of transmit electrodes coupled to a signal generator for transmitting a drive current into tissue around the marker, a set of receive electrodes configured to detect voltage signals within the tissue corresponding to impedance of the tissue in response to the drive current, a light source for delivering light pulses into the body to cause the energy converter to activate and deactivate the circuit to change the configuration of the antenna of the marker, and a processor coupled to the receive electrodes for processing the voltage signals to identify changes in the impedance that are synchronized with the light pulses to determine whether the marker is operating properly.

In accordance with still another embodiment, a method is provided for localization of a target tissue region within tissue that includes implanting a marker within tissue, the marker comprising an energy converter, and a circuit coupled to the energy converter and an antenna; placing an apparatus adjacent tissue oriented towards the marker; and activating the apparatus to a) transmit a drive current via drive electrodes into the tissue, b) receive voltage signals from the tissue via receive electrodes corresponding to impedance of the tissue, c) deliver light pulses into the tissue such that the energy converter transforms the light pulses to activate and deactivate the circuit to change a configuration of the antenna, and d) determine whether changes in the received voltage signals are synchronized with the light pulses to determine whether the marker is operating properly.

In accordance with yet another embodiment, a method is provided for localization of a target tissue region within tissue that includes implanting a marker within tissue, the marker comprising an energy converter, and a circuit coupled to the energy converter and an antenna; placing an apparatus adjacent tissue oriented towards the marker; and activating the apparatus to a) transmit an A/C drive current via drive electrodes into the tissue, b) receive voltage signals from the tissue via receive electrodes corresponding to impedance of the tissue, and c) process the voltage signals to remove an A/C component and identify an amplitude component of the voltage signals to determine a threshold voltage; and activating a light source of the apparatus to deliver light pulses into the tissue such that the energy converter transforms the light pulses to activate and deactivate the circuit to change a configuration of the antenna, whereupon the apparatus determines whether changes in the amplitude component of the received voltage signals relative to the threshold voltage are synchronized with the light pulses to determine whether the marker is operating properly.

Other aspects and features of the present invention will become apparent from consideration of the following description taken in conjunction with the accompanying drawings.

BRIEF DESCRIPTION OF THE DRAWINGS

These and other features, aspects, and advantages of the present disclosure will become better understood with regard to the following description, appended claims, and accompanying drawings where:

FIGS. 1A-1C are top, side, and end views, respectively, of an exemplary embodiment of a marker for implantation within a patient's body.

FIG. 2 is an exemplary embodiment of a schematic of a circuit that may be included in the marker of FIG. 1.

FIGS. 3A and 3B are schematics demonstrating operation of a switch of the circuit of FIG. 2.

DETAILED DESCRIPTION OF THE EXEMPLARY EMBODIMENTS

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Generally, systems and methods are provided for detecting a marker implanted within tissue. In particular, the systems and methods herein involve using an impedance reflection apparatus to confirm that a marker implanted within a patient's body is performing properly, e.g., has not been damaged since implantation. For example, during or after implantation of a marker within tissue, instruments may be used that may expose the marker to electrical energy. Modern breast surgery often involves the use of electro-cutting tools, electrocautery tools, and/or other tools (not shown), which can generate electrical pulses of a few kV. If such a tool gets close to a marker implanted within tissue, the tool can cause a very large voltage across antenna wires of the marker and potentially destroy a switch or other electrical circuitry of the marker.

Figure 4A:
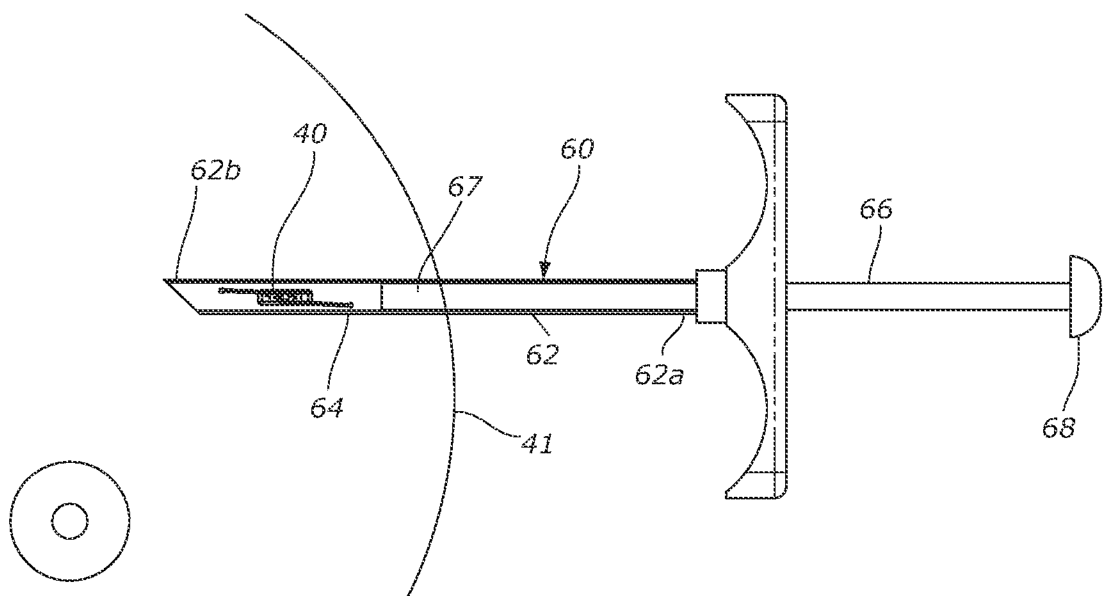
FIGS. 4A and 4B are side views of a breast, showing a delivery device being used to deliver a marker into tissue within the breast.
Figure 4B:
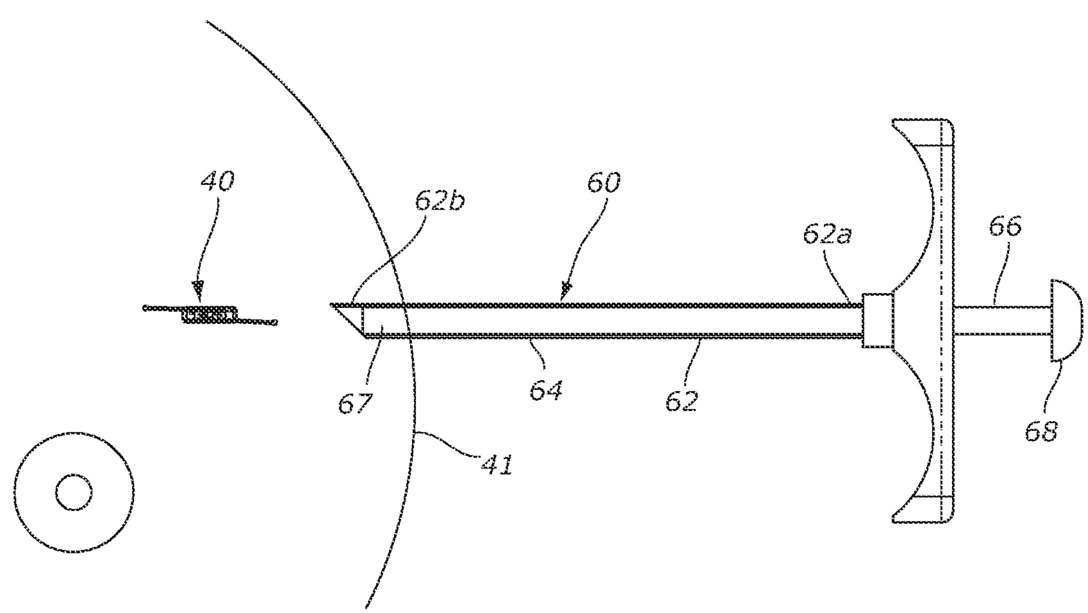

Turning to the drawings, FIGS. 1A-1C show an exemplary embodiment of a passive marker or tag 40 that may be implanted within a patient's body, such as within a breast 90, e.g., as shown in FIGS. 4A and 4B and described further below. Generally, the marker 40 includes an electronics package 42 coupled to one or more wires or other antennas 44. The marker 40 may be included in a system for performing a procedure, such as a lumpectomy procedure, e.g., including one or more of a delivery device 60 (not shown, see, e.g., FIGS. 4A-4B) for delivering one or more of the markers into tissue, an impedance reflector apparatus 110, such as that shown in FIGS. 5A-5D and described further elsewhere herein, and a probe (not shown) for locating marker(s) implanted within tissue, e.g., any of the probes and systems disclosed in U.S. Pat. No. 8,892,185 and U.S. Pat. No. 9,713,437, and U.S. Publication Nos. 2016/0354177 and 2017/0319102, the entire disclosures of which are expressly incorporated by reference herein.

Returning to FIGS. 1A-1C, in an exemplary embodiment, each antenna 44 may be an elongate member, e.g., a solid or hollow structure having a diameter or other maximum cross-section between about half and two millimeters (0.5-2 mm) and a length between about one and ten millimeters (1.0-10 mm). The antennas 44 may be formed from elastic or superelastic material and/or from shape memory material, e.g., stainless steel, Nitinol, and the like, such that the antennas 44 are biased to a predetermined shape when deployed within tissue, but may be elastically deformed, e.g., to facilitate delivery, as explained elsewhere herein. As described elsewhere herein, the antennas 44 may act to modify a resonance impedance of the marker and/or tissue within which the marker 40 is implanted, e.g., in response to radar or other electromagnetic signals that strike the marker 40, to enhance detecting and/or locating the marker 40 within a patient's body.

Optionally, the antennas 44 may carry one or more beads or other elements (not shown), e.g., similar to embodiments described in the patents and applications incorporated by reference herein. For example, the antennas 44 may include core wires that carry a plurality of beads or segments (not shown) including multiple surfaces, angles, and/or edges to enhance detection of the marker 40. In an exemplary embodiment, the beads may include a plurality of individual annular bodies, e.g., each defining a portion of a generally cylindrical or spherical shape.

As shown in FIGS. 1A-1C, the antennas 44 may be biased to assume a substantially linear configuration, e.g., such that the antennas 44 extend substantially parallel to a longitudinal axis 48 of the marker 40. Alternatively, the antennas 44 may be substantially rigid such that the marker 40 remains in a substantially fixed, e.g., linear or curved, shape. Optionally, one or both antennas 44 may be offset from the longitudinal axis 48, which may enhance loading the marker 40 within a delivery device (not shown), as described elsewhere herein or in the patents and applications incorporated by reference herein.

As best seen in FIG. 1A, each antenna 44 may include a first end 44*a* coupled to a printed circuit board (PCB) or other substrate 50 within the package 42 and a second free end 44*b* terminating in an enlarged and/or rounded tip 45. Optionally, the first ends 44*a* may include one or more bends, e.g., to facilitate coupling the first ends 44*a* to the substrate 50 and/or such that the antennas 44 extend tangentially from opposite sides of the package 42, as best seen in FIG. 1A.

Alternatively, the antennas 44 may be biased to assume a curvilinear or other configuration, e.g., a helical, serpentine or other curved shape (not shown), around the longitudinal axis 48. For example, the antennas 44 may be formed from elastic or superelastic material that is shape set such that the antennas 44 are biased to a helical configuration (not shown), yet may be resiliently straightened to a substantially linear configuration, e.g., to facilitate loading the marker 40 into a delivery device and/or otherwise introducing the marker 40 into a patient's body, e.g., as described in the patents and applications incorporated by reference herein.

With additional reference to FIG. 2, the marker 40 may include one or more circuits or other electrical components encased or embedded in the electronics package 42 and configured to modulate incident signals from a probe (not shown) used to locate the marker 40, also as described elsewhere herein or in the patents and applications incorporated by reference herein. For example, the components may be provided on a semiconductor chip, print circuit board (PCB), and/or other substrate 50 carried in the package 42. In an exemplary embodiment, the components may include a voltage or power source or other power or energy converter 52, a switch 54 that may be opened and closed when the energy converter 52 generate electrical energy, and an Electro Static Discharge (ESD) protection device 58, e.g., mounted or otherwise provided on the substrate 51.

The components may be encased within one or more components defining the package 42. In an exemplary embodiment, the components may be soldered, glued, or otherwise mounted on a surface of the substrate 50 and encapsulated in epoxy or other insulating and/or protective material (not shown). For example, the components may be mounted within the package 42 such that the components are electrically isolated from one another other than as coupled in the schematic of FIG. 2. Optionally, shrink tubing or other outer body may be applied around the epoxy material, e.g., to provide a desired finish and/or outer surface for the marker 40.

In an exemplary embodiment, the energy converter 52 includes a plurality of photosensitive diodes capable of transforming incident light (e.g., infrared light) striking them into electrical energy (e.g., a predetermined minimum voltage). As shown, multiple pairs of diodes 52 may be connected in series, which may be arranged orthogonally to one another spatially within the package 42. For example, given that photosensitive diodes are directional, at least two pairs of diodes 52 may be mounted within the package 42 offset one hundred eighty degrees (180°) or otherwise relative to one another, e.g., as best seen in FIG. 1A, such that at least one pair of diodes 52 may receive light from a light transmitter from the apparatus 110 or probe regardless of the orientation of the marker 40 relative to the apparatus 110 or probe after implantation. The package 42 may be at least partially transparent or the diodes 52 may be exposed such that light directed towards the package 42 may be received by the diodes 52.

Optionally, the diodes 52 and/or any surfaces of the package 42 overlying the diodes 52 may include one or more coatings, filters, and the like (not shown), e.g., formed on the shrink tubing or other components of the package 42, to limit the light that strikes the diodes 52 in a desired manner. For example, one or more coatings may be provided that only permit a desired band width of infrared light to strike the diodes 52. In this manner, multiple markers may be provided that allow different band widths to activate the respective markers, e.g., such that a probe may activate a desired marker by transmitting infrared red limited to the particular band width of the desired marker.

In alternative embodiments, the energy converter 52 may include other components capable of transforming external energy into a desired voltage. For example, if the apparatus 110 or probe includes another power source, e.g., a source of EMF, RF, or vibrational energy, the energy converter 52 may include a pick-up coil, antenna, or other device capable of transforming the incident energy into the desired voltage, e.g., including a capacitor and/or other components arranged to deliver the desired voltage to the switch 54. One advantage of infrared energy is that it may pass sufficiently through tissue such that an apparatus 110 or probe placed against a patient's skin may deliver sufficient energy to activate a relatively small marker 40 implanted several inches away within the patient's body, e.g., within a breast 90, as shown in FIGS. 6A-6D.

In the embodiment shown in FIG. 2, the switch 54 may be a field effect transistor (FET), e.g., a junction field effect transistor (JFET), with one end of the diodes 52 coupled to the gate (G) and the other coupled to the source (S), with a resistor 56 coupled between the gate (G) and the source (S), e.g., to discharge the diodes 52 when there is no IR light. In an exemplary embodiment, the switch 54 may include an enhancement mode pseudomorphic high electron mobility transistor (E-pHEMT), such as a VMMK-1225 manufactured by Avago Technologies US Inc., and the resistor 56 may be a three mega-Ohm (3MΩ) resistor. In an alternative embodiment, the switch 54 may be a Schottky diode coupled to the diodes 52 (or other voltage source), e.g., with opposite ends of the diode coupled to the antennas 44.

Also as shown, the source (S) of the switch 54 may be electrically coupled to one of the antennas 44 and the drain (D) may be coupled to the other antenna 44. The antennas 44 may be bonded or otherwise attached to the package 42 such that ends of the antennas 44 are electrically coupled to the switch 54 as shown.

Each diode 52 may be capable of generating sufficient voltage (e.g., about a half Volt (0.5 V)) when exposed to light to open and close the switch 54 when there is little or no load (i.e., current draw). Since the resulting circuit is intended to modulate signals from the probe, little or no current is needed, and so the power required from the diodes 52 (and consequently from the probe) may be minimal, thereby reducing power demands of the marker 40 and probe 1020.

With additional reference to FIGS. 3A and 3B, light intermittently striking the diodes 52 may generate a voltage across the gate (G) and source (S) to provide a control signal that may open and close the switch 54. For example, FIG. 3A shows the switch 54 in the open configuration when infrared light is absent, while FIG. 3B shows the switch 54 in the closed configuration when infrared light 70 strikes the diodes 52, thereby connecting both antennas 44 together. Thus, the result is that the marker 40 provides a passive reflector tag that includes what equates to a high-frequency switch in the middle of the marker 40. By being able to change the switch 54 from closed to open, the reflective properties of the effective antenna provided by the antennas 44 may be changed significantly. For example, the switch 54 may change the polarity or otherwise modulate signals reflected from the marker 40 as the switch 54 is opened and closed and/or may change a resonance impedance of the marker 40 and/or tissue within which the marker 40 is implanted.

Some of the challenges involved in detecting markers implanted within breast tissue (or elsewhere in a patient's body) include the relatively small radar cross-section (RCS) of such markers and contamination of the received reflected signal, e.g., due to (a) scattering caused by tissue inhomogeneity; (b) cross-talk between transmit and receive antennas of the probe; and (c) signal distortions due to near field effects and other factors. To deal with these complicating factors and distinguish the reflected marker signal from contaminating signals received by the probe, the switch 54 provides periodic modulation of reflective properties of the marker 40.

Specifically, the marker 40 is made to periodically change its structure between two form factors, e.g., the reflectors shown in FIGS. 3A and 3B. For example, as described further elsewhere herein, digital signal processing of the received signals using ultra-wideband (UWB) radar uses synchronous detection of the signal modulated with marker switching frequency. This significantly increases the signal-to-noise (SNR) on the marker signal because other contaminating signals remain unchanged within the modulation period. To provide a mechanism for a synchronous detector, the marker switching process is controlled in the probe (not shown) by illuminating breast tissue with near infrared (IR) light pulses that are received by the marker 40.

Switching of the marker reflective form-factor is controlled with the set of diodes 52 operating in photovoltaic mode. When the diodes 52 receive light from the probe 102 (represented by arrows 70 in FIG. 3B), the diodes 52 generate voltage that is applied between the gate (G) and source (S) of the switch 54, which closes and connects together the drain (D) and source (S) making both antenna wires 44 connected together, as shown in FIG. 3B. When the light is off, the switch 54 is open and the drain (D) and source (S) are electrically disconnected, as shown in FIG. 3A.

In addition, the ESD device 58 may be coupled in parallel across the switch 54, e.g., between the drain (D) and source (S), to provide protection against an electrostatic discharge event. For example, use of an E-pHEMT device as switch 54 sets restrictions on the absolute maximal voltage between the drain (D) and source (S) and, therefore, across the marker's antennas. In the exemplary embodiment of a VMMK-1225 E-pHEMT, the maximal voltage across the switch 54 may be no more than about five Volts (5 V). To increase survivability of the marker 40, the ESD protection device 58 truncates voltage on the switch 58 device when the voltage approaches the maximal value. Generally, the ESD protection device 58 in the marker 40 should have low capacitance that does not shunt the antennas 44 for the frequency range of the small amplitude UWB signal coming from the signals from the probe 1020. In exemplary embodiments, the ESD protection device 58 may be a transient voltage suppressor, such as a Zener diode, a low-capacitance varistor, and the like.

Turning to FIGS. 4A and 4B, a needle or delivery device 60 may be provided for introducing one or more markers (one marker 40 shown) into a patient's body, e.g., similar to any of the embodiments described in the patents and applications incorporated by reference herein. For example, the delivery device 60 may include a shaft 62 including a proximal end 62*a* and a distal end 62*b* sized for introduction through tissue into a target tissue region (not shown) and carrying the marker(s) 40. The delivery device 60 may include a lumen 64 extending at least partially between the proximal and distal ends 62*a*, 62*b* of the shaft 62, and a pusher member 66 slidable within the shaft 62 for selectively delivering one or more markers 40 successively or otherwise independently from the lumen 64.

As shown, the distal end 62*b* of the shaft 62 may be beveled, pointed, and/or otherwise sharpened such that the shaft 62 may be introduced directly through tissue. Alternatively, the delivery device 60 may be introduced through a cannula, sheath, or other tubular member (not shown) previously placed through tissue, e.g., as described in the applications incorporated by reference herein. Optionally, the distal end 62*b* may include a band or other feature, e.g., formed from radiopaque, echogenic, or other material, which may facilitate monitoring the distal end 62*b* during introduction, e.g., using fluoroscopy, ultrasound, electromagnetic signals, and the like.

As shown, the pusher member 66 includes a piston or other element (not shown) disposed within the lumen 64 adjacent the marker(s) 40 and a plunger or other actuator 68 coupled to the piston to push the marker(s) 40 from the lumen 64. For example, as shown in FIG. 4A, the distal end 62*a* of the shaft 62 (carrying the marker 40 therein) may be inserted into the breast 41 (or other tissue) and advanced or otherwise positioned to place the marker 40 at a target location, e.g., within a cancerous lesion (not shown). Optionally, external imaging may be used to confirm the location of the marker 40 relative to the lesion. Once at the target location, the shaft 62 may be withdrawn relative to the pusher member 66, thereby deploying the marker 40, as shown in FIG. 4B. Optionally, the delivery device 60 may carry multiple markers (not shown), and the shaft 62 may be repositioned one or more times to deploy additional markers.

Alternatively, if desired, the pusher member 66 may be advanced to deploy the marker 40 from the lumen 64, rather than retracting the shaft 62. In another alternative, a trigger device or other automated actuator (not shown) may be provided on the proximal end 62*a* of the shaft 62, which may retract the shaft 62 sufficiently with each activation, e.g., to delivery an individual marker 40 from the distal end 62*b*, e.g., as described in the applications incorporated by reference herein.

Figure 5A:
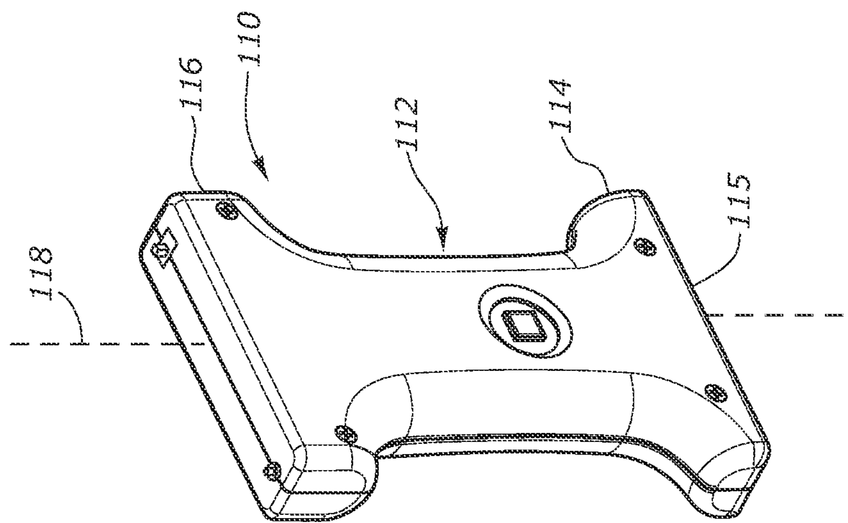
FIGS. 5A-5C are perspective, side, and end views, respectively, of an exemplary embodiment of an impedance reflector detection apparatus.
Figure 5B:
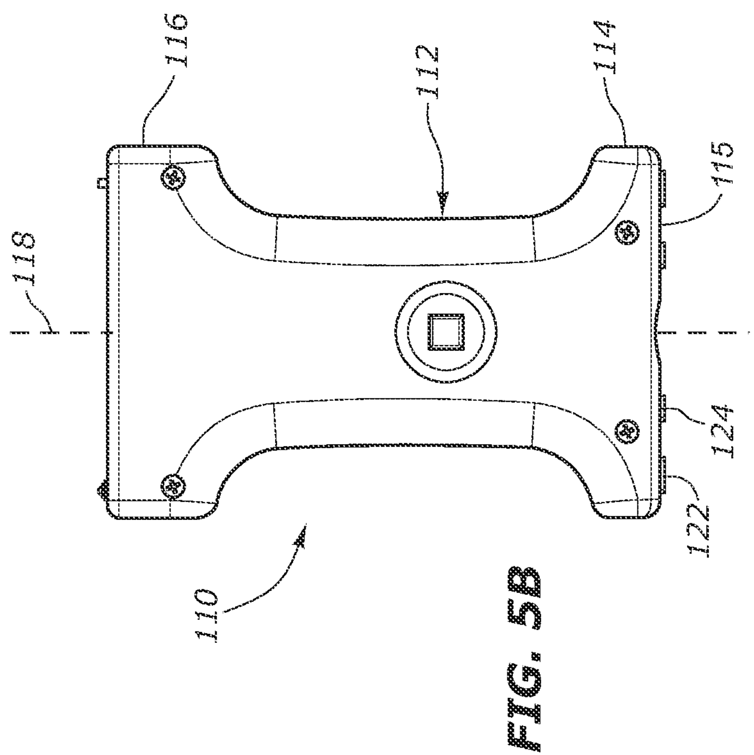
Figure 5C:
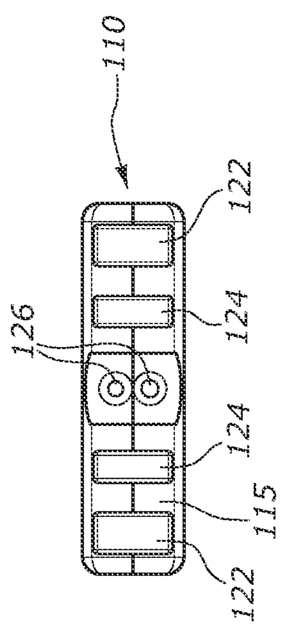
Figure 5D:
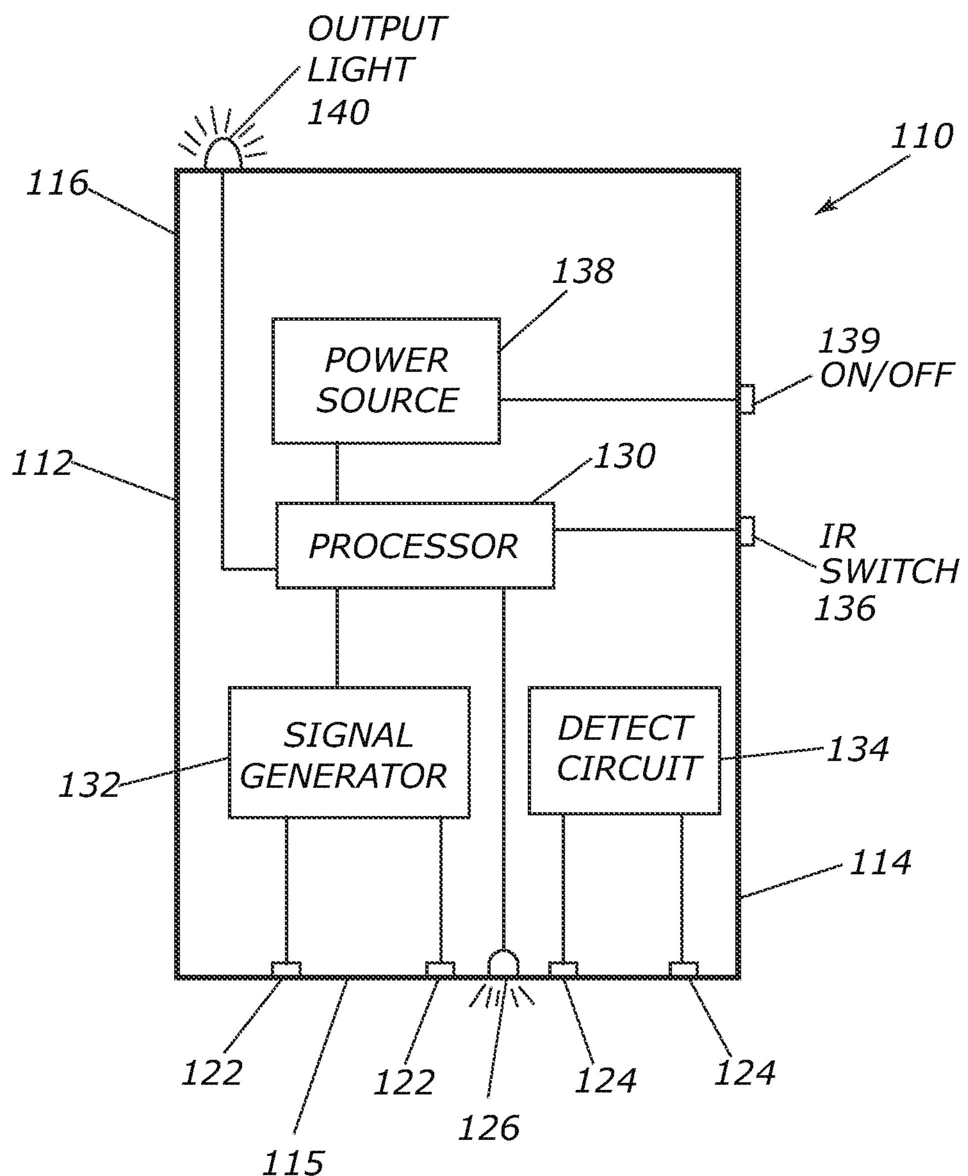
FIG. 5D is a schematic showing exemplary components of the apparatus of FIGS. 5A-5C.
Figure 6A:
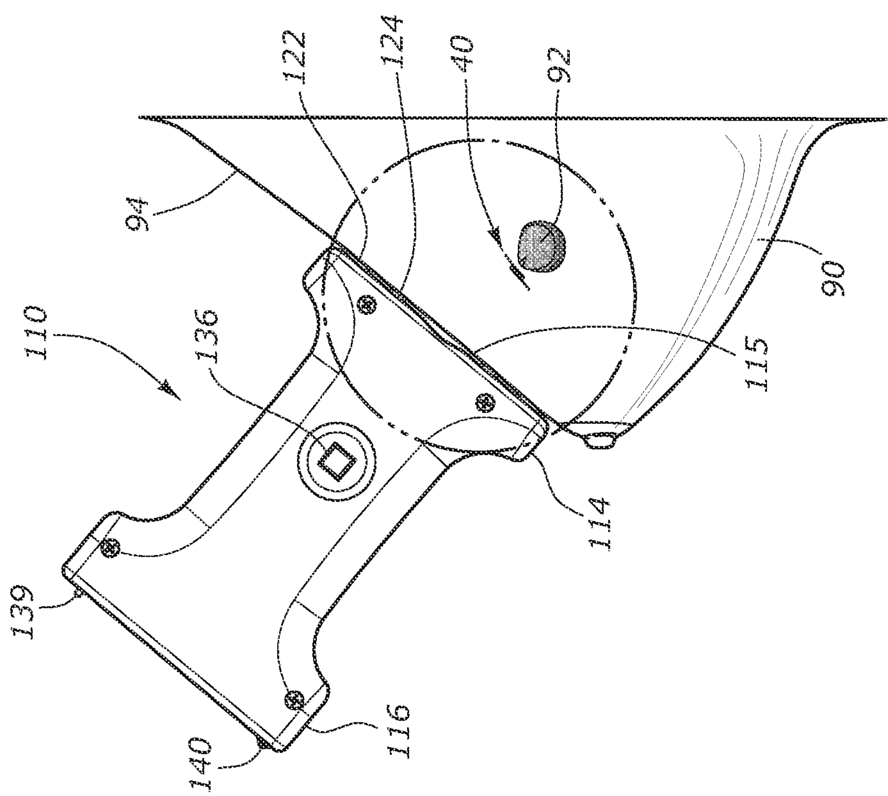
FIGS. 6A-6D show an exemplary method for detecting a marker implanted adjacent a lesion using an apparatus, such as the apparatus shown in FIGS. 5A-5C.
Figure 6B:
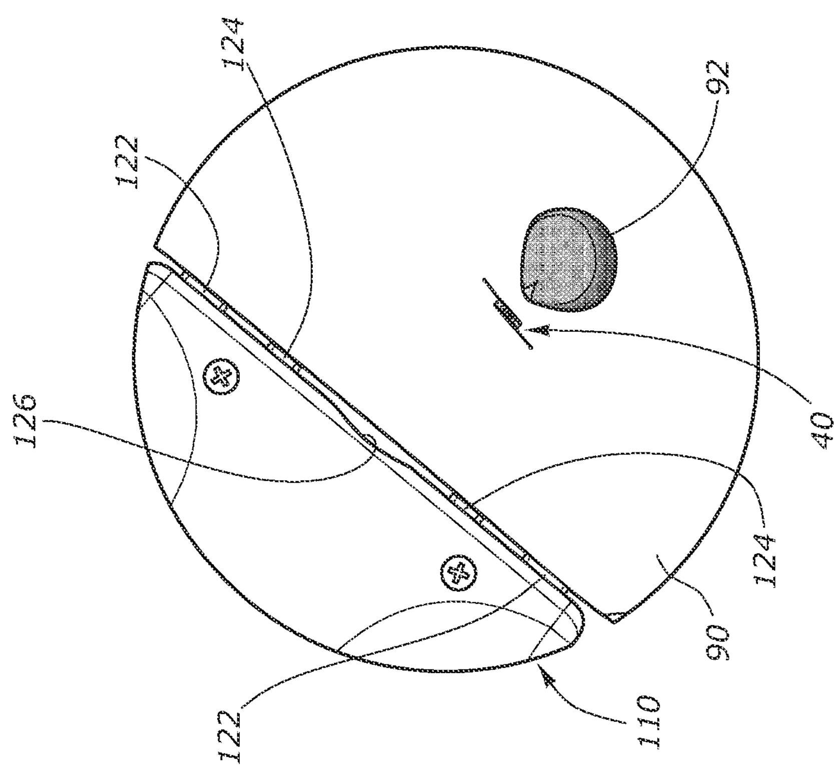
Figure 6C:
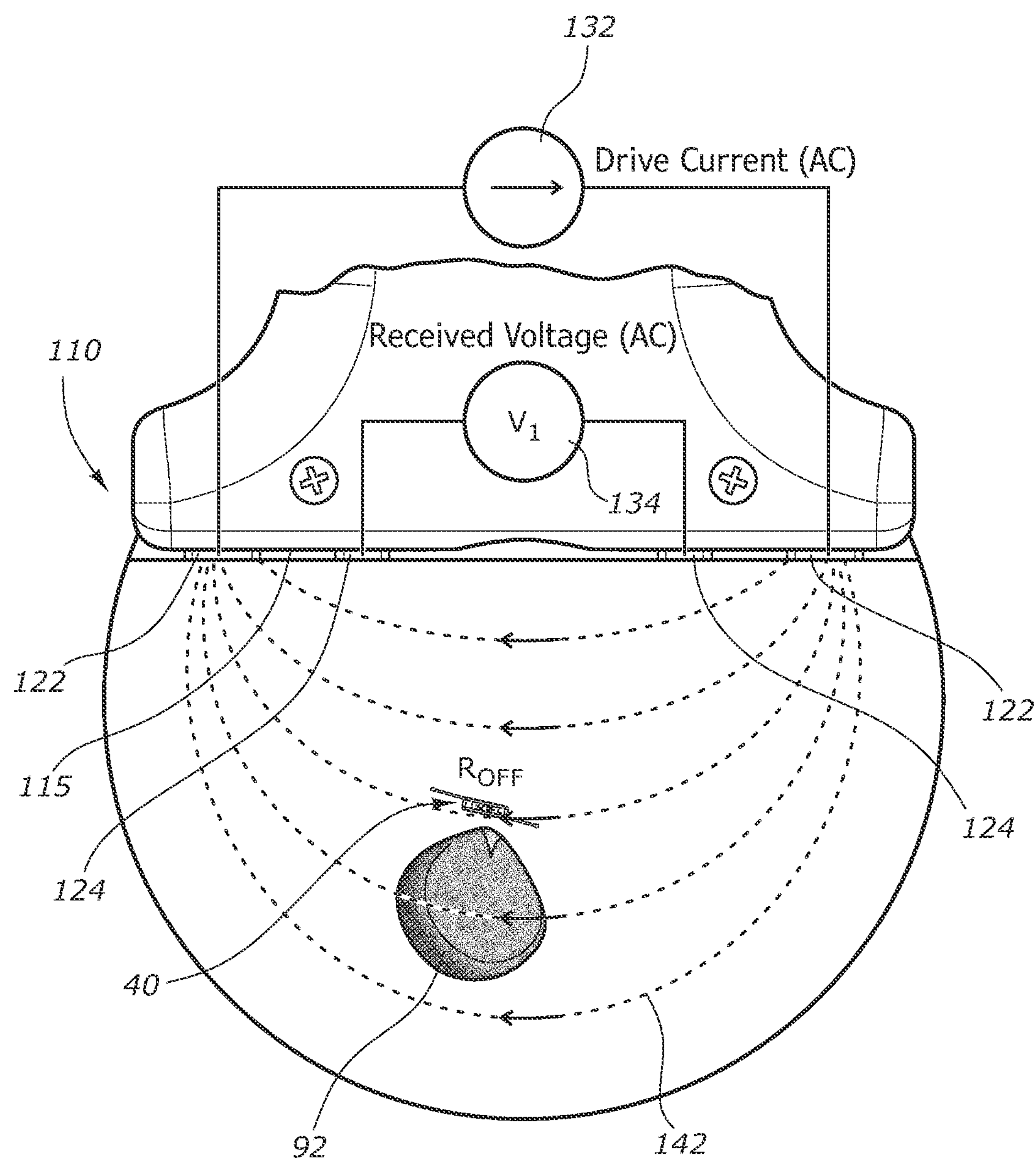
Figure 6D:
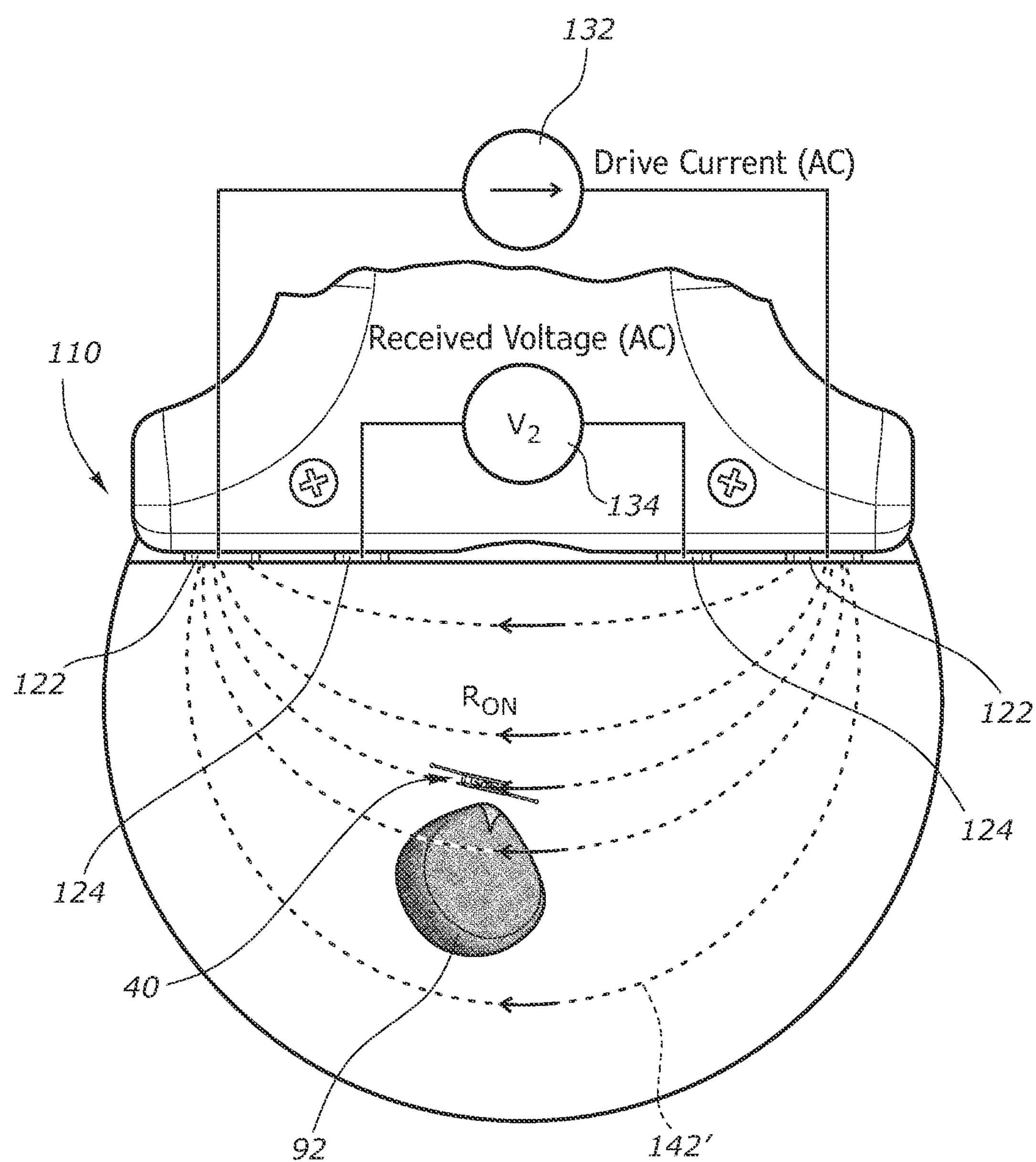

Turning to FIGS. 5A-5D, an exemplary embodiment of an impedance reflector apparatus 110 is shown that may be used to detect a marker implanted within tissue, e.g., as shown in FIGS. 6A-6D and described further elsewhere herein. Generally, the apparatus 110 is a portable, handheld device that includes a housing 112 containing internal components, e.g., as shown in FIG. 6D, and including a first or distal end 114 defining a patient contact surface 115 intended to be placed against tissue, e.g., a flat surface for contacting a patient's skin, and a second or proximal end 116. As best seen in FIG. 5C, the patient contact surface 115 may include one or more components for transmitting and/or receiving signals to detect the marker 40, for example, one or more electrodes, e.g., a pair of drive electrodes 122 and a pair of receive electrodes 124, and a light transmitter, e.g., one or more light emitting diodes (LEDs) 126, configured to transmit light pulses into tissue contacted by the distal end 1024, e.g., into breast tissue 90, as described further elsewhere herein. Alternatively, the light transmitter may include one or more LEDs within the housing 112 and one or more light fibers, lenses, and the like to direct the light from the LED(s) from the patient contact surface 115 in a desired direction and beam configuration.

In an exemplary embodiment, the LEDs 126 are configured to deliver near infrared light between, for example, eight hundred and nine hundred fifty nanometers (800-950 nm) wavelength. Optionally, the LEDs 126 may include one or lenses, filters, and the like (not shown), if desired, for example, to focus the light transmitted by the apparatus 110 in a desired manner, e.g., in a relatively narrow beam extending substantially parallel to a longitudinal axis 118 of the housing 112, in a wider beam, and the like.

Alternatively, the apparatus 110 may include other energy sources instead of the light transmitter 126. For example, a source of electromagnetic energy, radiofrequency (RF) energy, vibrational energy, and the like (not shown) may be provided on the patient contact surface 115 for delivering energy pulses to selectively activate the marker 40, as described elsewhere herein. The energy source(s) may be pulsed in a predetermined manner, e.g., to cause the circuits of the marker 40 to be alternately activated and deactivated.

The apparatus 110 may include electrical components within the housing 112 for operating the apparatus 110, e.g., including one or more controllers, processors, signal generators, and the like (not shown) needed to generate signals for transmission by the drive electrodes 122 and/or to process signals received from the receive electrodes 124. These components may include discrete components, solid state devices, programmable devices, software components, and the like, as desired.

Figure 7A:
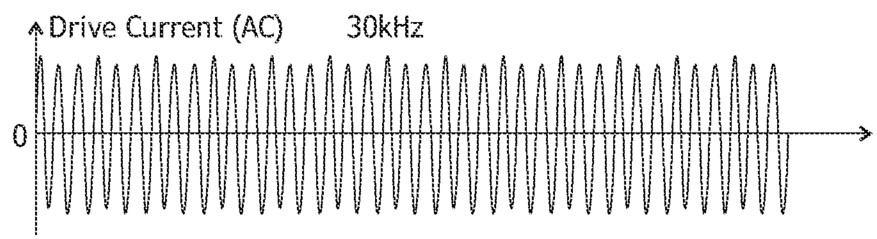
FIGS. 7A-7D are graphs showing the temporal relationship of transmitted voltages, infrared light transmission, detected voltages, and processed signals during use of the apparatus of FIGS. 5A-6D.
Figure 7B:
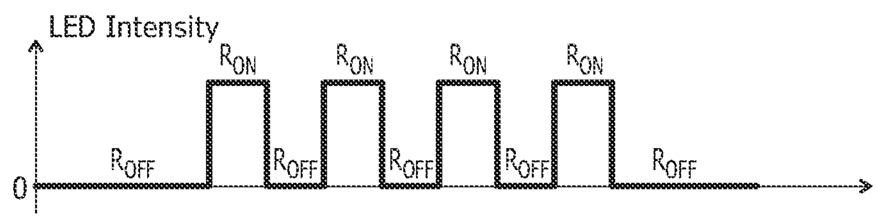
Figure 7C:
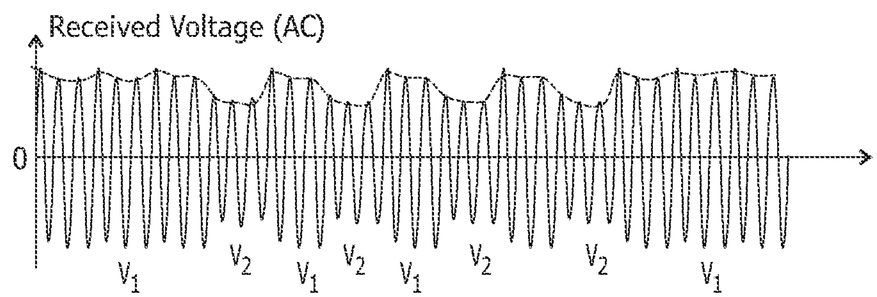

For example, as shown in FIG. 5D, the apparatus 110 may include a processor 130 configured to operate the various components, e.g., coupled to a signal generator 132 coupled to the drive electrodes 122, a detector circuit 134 coupled to the receive electrodes 124, and the LEDs 126. As shown in FIG. 7A, the signal generator 132 may be configured to generate a continuous, substantially uniform amplitude alternating current (when activated) at a relatively low frequency, e.g., between about three and three hundred kilohertz (3-300 kHz), e.g., at about thirty kilohertz (30 kHz). The signal generator 132 may be coupled to the drive electrodes 122 to generate a desired electromagnetic field within the tissue containing the marker 40. The receive electrodes 124 may be configured to measure the resulting voltage within the tissue in response to the A/C drive current, e.g., as shown in FIG. 7C, which is processed and/or communicated to the processor 130 by the detect circuit 134. The voltage signals may correspond to the impedance of the tissue adjacent the patient contact surface 115, which may be modified by the marker 40, as described further elsewhere herein. The processor 130 may also be coupled to the LEDs 126 to alternately activate and deactivate the LEDs 126 (e.g., after activating IR switch 136) to generate pulses of light transmitted at a predetermined frequency, e.g., substantially slower than the frequency of the drive current, as shown in FIG. 7C.

The processor 130 may be coupled to an output device, e.g., light 140, for displaying information to a user of the apparatus 110. For example, the processor 130 may process signals from the receive circuit 134 to determine whether a marker 40 has been detected and/or identified as operating properly. If so, the light 140 may be activated, thereby enabling a user to quickly confirm that the marker 40 may be used by a probe (not shown) to provide spatial or image data of the marker 40 and an associated lesion during a medical procedure, e.g., a lumpectomy procedure, as described further elsewhere herein.

The processor 130 may be coupled to a power source 138, e.g., a battery, or a cable for connecting the apparatus 110 to an external power source (not shown). In addition, one or more switches may be provided for activating various components of the apparatus 110 in a desired manner. For example, a main power switch 139 may be coupled to the power source 138 and/or processor 130 for providing power to the processor 130 and/or other components, and an IR switch 136 may be provided that may be used to selectively activate the LEDs 126, as described further below.

Turning to FIGS. 6A-6D, the apparatus may be used before, during, and/or after a medical procedure, e.g., after implanting a marker 40 within tissue, for example, adjacent a lesion 92 within a breast 90. For example, before the procedure, a target tissue region, e.g., a tumor or other lesion, may be identified using conventional methods. For example, a lesion (not shown) within a breast 90 may be identified, e.g., using mammography and/or other imaging, and a decision may be made to remove the lesion.

Once the lesion 92 has been identified, one or more markers may be implanted within the tissue, e.g., identifying a desired margin or region around the lesion in advance of the lumpectomy procedure. For example, as shown in FIG. 6A, a marker 40 has been implanted within breast tissue adjacent a lesion 92 identified to be removed by lumpectomy, e.g., using a needle or other delivery device, such as that shown in FIGS. 5A-5B. It will be appreciated that multiple markers (not shown) may be implanted around the lesion 92, as desired, e.g., as described elsewhere herein and in the patents and applications incorporated by reference herein.

The apparatus 110 may be used immediately after implanting the marker 40 within the breast 90 to confirm that the marker 40 was not damaged during implantation, e.g., that the switch 52 and/or other electrical components are operating properly. In addition, because the patient may undergo other treatments before the actual lumpectomy procedure, the apparatus 110 may be used as often as desired to confirm that the marker 40 remains functioning properly. Optionally, the apparatus 110 may be used during the lumpectomy procedure to confirm that instruments used during the procedure have not damaged the marker 40.

Turning to FIGS. 6A and 6B, during use, initially the patient contact surface 115 of the apparatus 110 may be placed against the patient's skin generally overlying the lesion 92 and marker implanted within the breast 90. At any time, the main switch 139 may be actuated to turn the apparatus 110 on, e.g., to provide power to the processor 130, whereupon the signal generator 132 and detect circuit 134 may be activated. For example, as shown in FIG. 6C, the signal generator 132 has been activated and providing an A/C drive current, e.g., such as that shown in FIG. 7A, between the drive electrodes 122, thereby creating an electrical circuit with current flowing through the tissue around the marker 40 between the electrodes 122 (as represented by dashed lines 142). The detect circuit 124 receives voltage signals from the receive electrodes 124 in response to the drive current, e.g., such as that shown in FIG. 7C in the $R_{off}$ region identified by $V_1$. The processor 130 may processor the voltage signals, e.g., to remove the A/C component and determine a baseline or threshold amplitude. Optionally, the processor 130 may provide an output, e.g., activate the light 140 or emit an audible sound to confirm that the threshold has been determined.

Turning to FIG. 6D, after sufficient time (or indication by the processor 130), the user may actuate the IR switch 136, whereupon the processor 130 may activate the LEDs 136 to generate pulses of infrared light (represented by dashed lines 144) into the tissue towards the marker 40. FIG. 7B shows an exemplary square wave representing periodic light pulses that may be generated by activation and deactivation of the LEDs 136 and transmitted into the tissue synchronized with the drive current delivered by the drive electrodes 122. The pulsed light from the LEDs 136 causes the switch 54 to open and close, thereby changing the form factor of the antennas 44, as described elsewhere herein.

Figure 7D:
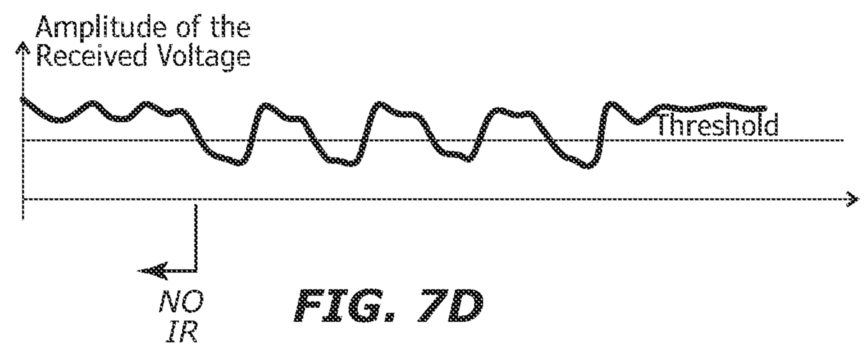

As shown in FIG. 6D, the switching of the marker 40 changes the impedance of the surrounding tissue, thereby changing the current flow (represented by dashed lines 142') between the drive electrodes 122, and modulating the voltage signals detecting by the receive electrodes 124, as demonstrated in FIG. 7C. As shown in FIG. 7D, the processor 130 may process the voltage signals, e.g., to remove the A/C component and provide an output representing the amplitude of the received signals. By comparing the amplitude to the threshold, the processor 130 may identify that the amplitude is alternating between two voltages synchronized with the light pulses from the LEDs 126 (e.g., V1 with the LEDs 126 off and V2 with the LEDs on, as shown in FIG. 7C). Once the processor 130 confirms this synchronized response, the processor 130 may provide an output, e.g., activating light 140 and/or emitting an audible signal, to provide confirmation to the user that the marker 40 is responding properly and therefore the electrical components of the marker 40 are not damaged. Once the user receives this confirmation, they may deactivate the IR switch 136, remove the apparatus 110 from contacting the breast 90 and, if desired, turn the apparatus 110 off using main switch 139.

Optionally, the apparatus 110 may be used to confirm that multiple markers 40 (not shown) implanted within tissue are each operating properly and not damaged. For example, as described above, each marker may include a filter that allows only a distinct narrow bandwidth of light to strike that marker's photodiodes. In this embodiment, the apparatus 110 may include multiple LEDs configured to transmit light at one of the narrow bandwidths at a time, thereby allowing a user to detect each marker in turn. Alternatively, the apparatus 110 may include a set of LEDs configured to transmit a relatively broad bandwidth of light, and a set of filters that may be actuated within the apparatus 110 to narrow the bandwidth actually transmitted from the patient contact surface 115 to one of the narrow bandwidths corresponding to a respective marker.

In a further alternative, each marker 40 may include a processor configured to analyze light pulses from the apparatus 110 to identify a predetermined bit code in the light pulses. The processor 130 of the apparatus 110 may be capable of including one of the bit codes in the light pulses to selectively activate and detect the marker associated with the transmitted bit code, e.g., similar to the markers and probes described in U.S. Publication No. 2017/0319102, incorporated by reference herein, thereby allowing the apparatus 110 to confirm whether each of the markers is operating properly. In these alternatives, the apparatus 110 may include an interface that allows the user to select one of the markers to be detected and then use the apparatus 110 to detect that marker, switch to a different marker, etc.

Optionally, the apparatus 110 may be used during a breast biopsy or lumpectomy procedure, e.g., to facilitate localization of a lesion or other target tissue region and/or to facilitate dissection and/or removal of a specimen from a breast 90 or other body structure. For example, the processor 130 may be configured to process the received voltage signals to determine a distance component based on the impedance corresponding to the distance from the patient contact surface 115 to the marker. For example, the apparatus 110 may include or be coupled to a display (not shown) providing distance, angle, orientation, and/or other data based on predetermined criteria, e.g., based on the relative distance from the marker 40 to the apparatus 110. The distance information may be displayed as a numerical value representing the distance in units of length, such as in inches (in.) or centimeters (cm). In addition or alternatively, the apparatus 1110 may include a speaker (also not shown) that may produce an audible indication of distance, e.g., spaced-pulses that increase in speed as the apparatus 110 is closer to the marker 40. Tissue may then be dissected, e.g., by creating an incision in the patient's skin and dissecting intervening tissue to a desired depth, e.g., corresponding to a target margin around the lesion is reached, while using the apparatus 110 to confirm the location of the marker 40. A tissue specimen may be excised or otherwise removed using conventional lumpectomy procedures, e.g., with the marker 40 remaining within the removed specimen.

It should be noted that, although the apparatus 110 is described as being particularly useful in detecting markers within breast lesions, the apparatus 110 may also be used in localization of other objects in other areas of the body, e.g., as described in the applications incorporated by reference herein.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for detecting a marker implanted within tissue that includes an energy converter coupled to a circuit for changing a configuration of an antenna of the marker, the apparatus comprising:

a set of transmit electrodes coupled to a signal generator for transmitting an A/C drive current into tissue around the marker;

a set of receive electrodes configured to detect voltage signals within the tissue corresponding to impedance of the tissue in response to the A/C drive current;

a light source for delivering light pulses into the body to cause the energy converter to activate and deactivate the circuit to change the configuration of the antenna of the marker; and a processor coupled to the receive electrodes for processing the voltage signals to identify changes in the impedance that are synchronized with the light pulses to determine whether the marker is operating properly, wherein the signal generator is configured to generate the A/C drive current with a substantially uniform amplitude, and wherein the processor is configured to remove an A/C component from the voltage signals to identify an amplitude component of the detected voltage signals, the processor configured to identify when the amplitude component of the detected voltage signals changes in synchronization with the light pulses to determine that the circuit of the marker is undamaged.

2. The apparatus of claim 1, further comprising an output device coupled to the processor that provides an indication when the processor determined the marker is operating properly.

3. The apparatus of claim 2, wherein the output device comprises at least one of a light and a speaker.

4. The apparatus of claim 1, further comprising an actuator for activating the light source to deliver the light pulses, the processor configured to process the detected voltage signals before activating the light source to determine a threshold voltage and to process the detected voltage signals after the light source is activated to identify changes relative to the threshold voltage.

5. The apparatus of claim 1, wherein the signal generator is configured to generate an alternating current between about three and three hundred kilohertz (3-300 kHz) for causing the transmit electrodes to transmit the A/C drive current.

6. The apparatus of claim 1, wherein the transmit electrodes and the receive electrodes are provided on a patient contact surface, and wherein the light source is configured to deliver the light pulses from the patient contact surface.

7. The apparatus of claim 6, wherein the patient contact surface is flat.

8. A system for localization of a target tissue region within tissue, comprising:

a marker sized for implantation within tissue comprising an energy converter coupled to a circuit for changing a configuration of an antenna of the marker; and an apparatus comprising a set of transmit electrodes coupled to a signal generator for transmitting an A/C drive current into tissue around the marker, a set of receive electrodes configured to detect voltage signals within the tissue corresponding to impedance of the tissue in response to the A/C drive current, a light source for delivering light pulses into the body to cause the energy converter to activate and deactivate the circuit to change the configuration of the antenna of the marker, and a processor coupled to the receive electrodes for processing the voltage signals to identify changes in the impedance that are synchronized with the light pulses to determine whether the marker is operating properly, wherein the signal generator is configured to generate the A/C drive current with a substantially uniform amplitude, and wherein the processor is configured to remove an A/C component from the voltage signals to identify an amplitude component of the detected voltage signals, the processor configured to identify when the amplitude component of the detected voltage signals changes in synchronization with the light pulses to determine that the circuit of the marker is undamaged.

9. The system of claim 8, further comprising an output device coupled to the processor that provides an indication when the processor determined the marker is operating properly.

10. The system of claim 9, wherein the output device comprises at least one of a light and a speaker.

11. The system of claim 8, further comprising an actuator for activating the light source to deliver the light pulses, the processor configured to process the detected voltage signals before activating the light source to determine a threshold voltage and to process the detected voltage signals after the light source is activated to identify changes relative to the threshold voltage.

12. The system of claim 8, wherein the signal generator is configured to generate an alternating current between about three and three hundred kilohertz (3-300 kHz) for causing the transmit electrodes to transmit the A/C drive current.

13. The system of claim 8, wherein the transmit electrodes and the receive electrodes are provided on a patient contact surface, and wherein the light source is configured to deliver the light pulses from the patient contact surface.

14. The system of claim 13, wherein the patient contact surface is flat.

15. The system of claim 8, wherein the apparatus comprises a transmit antenna configured to transmit a transmit signal into the body towards the marker, a receive antenna configured to receive a receive signal that is reflected from the marker, and wherein the light source is configured to deliver the light pulses into the body to open and close the circuit and modulate signals reflected by the marker back to the receive antenna;

wherein the processor is coupled to the receive antenna for locating the marker within the body based at least in part on the modulated signals reflected by the marker; and an output device to present information representing the distance from the tip of the probe to the marker.

16. The system of claim 15, wherein the energy converter comprises one or more photosensitive diodes configured to convert light from the light source to generate a voltage to open and close the circuit.

17. A method for localization of a target tissue region within tissue, comprising:

implanting a marker within tissue, the marker comprising an energy converter, and a circuit coupled to the energy converter and an antenna;

placing an apparatus adjacent tissue oriented towards the marker; and activating the apparatus to a) transmit an A/C drive current via drive electrodes into the tissue, b) receive voltage signals from the tissue via receive electrodes corresponding to impedance of the tissue in response to the A/C drive current, c) deliver light pulses into the tissue such that the energy converter transforms the light pulses to activate and deactivate the circuit to change a configuration of the antenna, and d) determine whether changes in the received voltage signals are synchronized with the light pulses to determine whether the marker is operating properly, wherein the A/C drive current has a substantially uniform amplitude, and wherein the apparatus removes an A/C component from the voltage signals to identify an amplitude component of the voltage signals and identifies when the amplitude component of the voltage signals changes in synchronization with the light pulses to determine that the circuit of the marker is undamaged.

18. The method of claim 17, wherein the apparatus provides an output indicating whether the marker is operating properly.

19. The method of claim 18, wherein the output comprises at least one of activating a light on the apparatus and emitting a predetermined sound from a speaker of the apparatus indicating whether the marker is operating properly.

20. The method of claim 17, wherein the apparatus initially activates the light source to deliver the light pulses before activating the light source to determine a threshold voltage and process the detected voltage signals after the light source is activated to identify changes relative to the threshold voltage.

21. The method of claim 17, wherein the apparatus comprises a signal generator that generates an alternating current between about three and three hundred kilohertz (3-300 kHz) to cause the transmit electrodes to transmit the drive current.

22. The method of claim 17, wherein the transmit electrodes and the receive electrodes are provided on a patient contact surface of the apparatus and the light source is configured to deliver the light pulses from the patient contact surface, and wherein placing the apparatus comprises placing the patient contact surface against the patient's skin before activating the apparatus.

23. A method for localization of a target tissue region within tissue, comprising:

implanting a marker within tissue, the marker comprising an energy converter, and a circuit coupled to the energy converter and an antenna;

placing an apparatus adjacent tissue oriented towards the marker; and activating the apparatus to a) transmit an A/C drive current via drive electrodes into the tissue, b) receive voltage signals from the tissue via receive electrodes corresponding to impedance of the tissue, and c) process the voltage signals to remove an A/C component and identify an amplitude component of the voltage signals to determine a threshold voltage; and activating a light source of the apparatus to deliver light pulses into the tissue such that the energy converter transforms the light pulses to activate and deactivate the circuit to change a configuration of the antenna, whereupon the apparatus determines whether changes in the amplitude component of the received voltage signals relative to the threshold voltage are synchronized with the light pulses to determine whether the marker is operating properly.

24. The method of claim 23, wherein the apparatus activates an output device when the changes in the amplitude component of the received voltage signals relative to the threshold voltage are synchronized with the light pulses to confirm that the marker is operating properly.

25. The method of claim 23, wherein the apparatus comprises a signal generator that generates an alternating current between about three and three hundred kilohertz (3-300 kHz) to cause the transmit electrodes to transmit the drive current.

26. The method of claim 23, wherein the transmit electrodes and the receive electrodes are provided on a patient contact surface of the apparatus and the light source is configured to deliver the light pulses from the patient contact surface, and wherein placing the apparatus comprises placing the patient contact surface against the patient's skin before activating the apparatus.

* * * * *